United States Patent [19]

Streczyn et al.

[11] 4,254,081
[45] Mar. 3, 1981

[54] BLOOD OXYGENATOR

[75] Inventors: Michael V. Streczyn, Huntington Beach; Ronald B. Luther, Newport Beach; Daniel L. Doyle, Murietta, all of Calif.

[73] Assignee: Research Partners Limited, Hayward, Calif.

[21] Appl. No.: 77,661

[22] Filed: Sep. 21, 1979

[51] Int. Cl.³ .............................................. A61M 1/03
[52] U.S. Cl. ......................................... 422/46; 422/47
[58] Field of Search ................................... 422/46, 47

[56] References Cited

U.S. PATENT DOCUMENTS

| | | | |
|---|---|---|---|
| 3,291,568 | 12/1966 | Sautter | 422/46 |
| 3,488,158 | 1/1970 | Bentley et al. | 422/46 X |
| 4,065,264 | 12/1977 | Lawin | 422/46 |
| 4,138,288 | 2/1979 | Lewin | 422/46 X |
| 4,138,464 | 2/1979 | Lewin | 422/46 |
| 4,140,635 | 2/1979 | Remond | 422/47 X |
| 4,160,801 | 7/1979 | Budolato et al. | 422/47 X |

FOREIGN PATENT DOCUMENTS 1410495 10/1975 United Kingdom ...................... 422/47

Primary Examiner—Barry Richman
Attorney, Agent, or Firm—Willie Krawitz

[57] ABSTRACT

An oxygenator for blood employs a unique and inexpensive, tubular, finned heat exchanger, one type utilizing a spirally wound plate attached to the tube, and another type comprising longitudinal fins. The oxygenator provides a fairly uniform oxygen saturation which permits better control over the oxygen content in a patient's blood. Also, elevated inlet oxygen pressures can be reduced, and this lessens the possibility of embolii due to cavitation effects when $CO_2$ is released by the blood following oxygenation.

A preferred form of a sparger for inlet oxygen to the blood is made of a porous, hydrophobic plastic material such as high density polyethylene.

19 Claims, 9 Drawing Figures

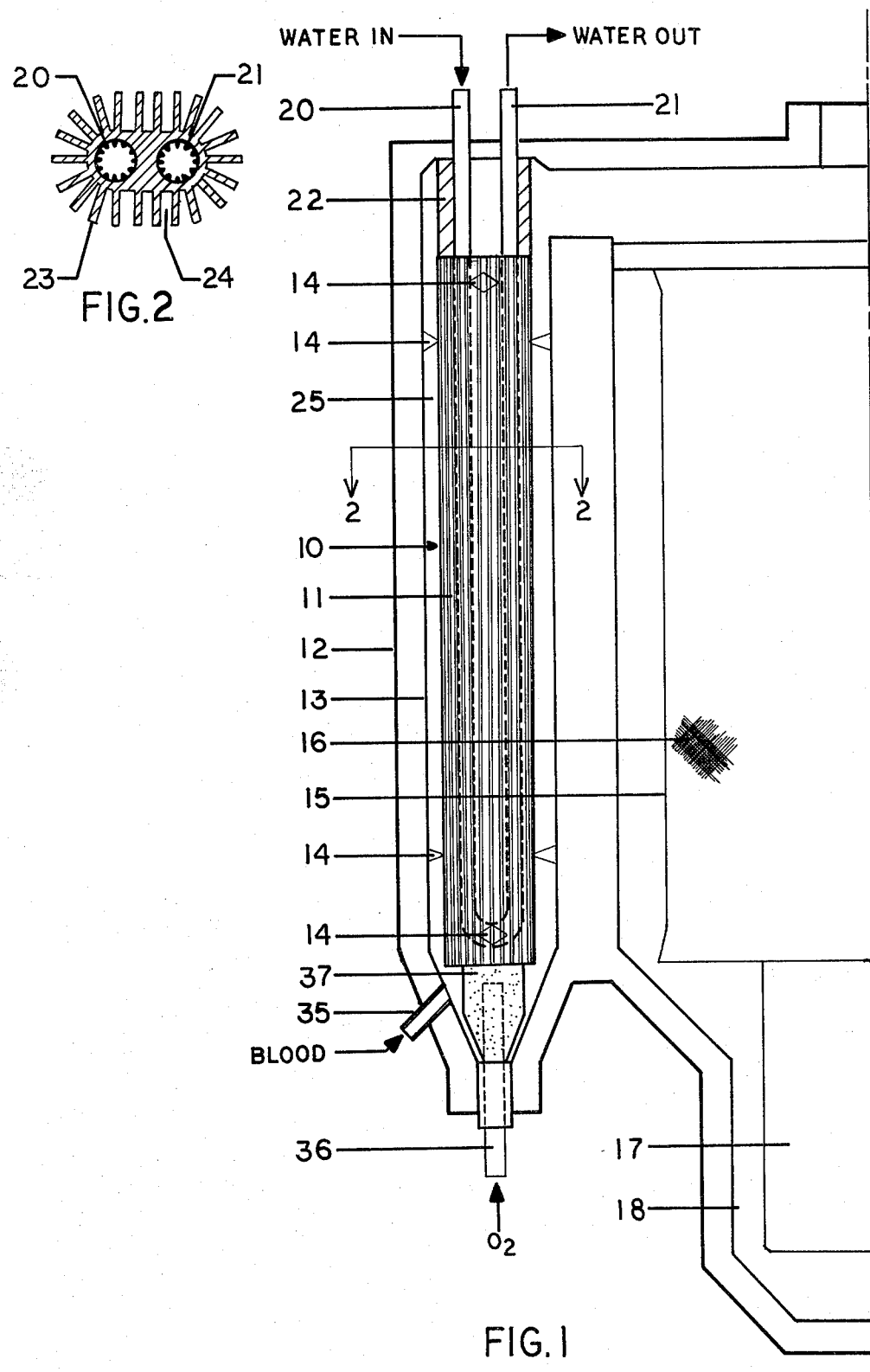

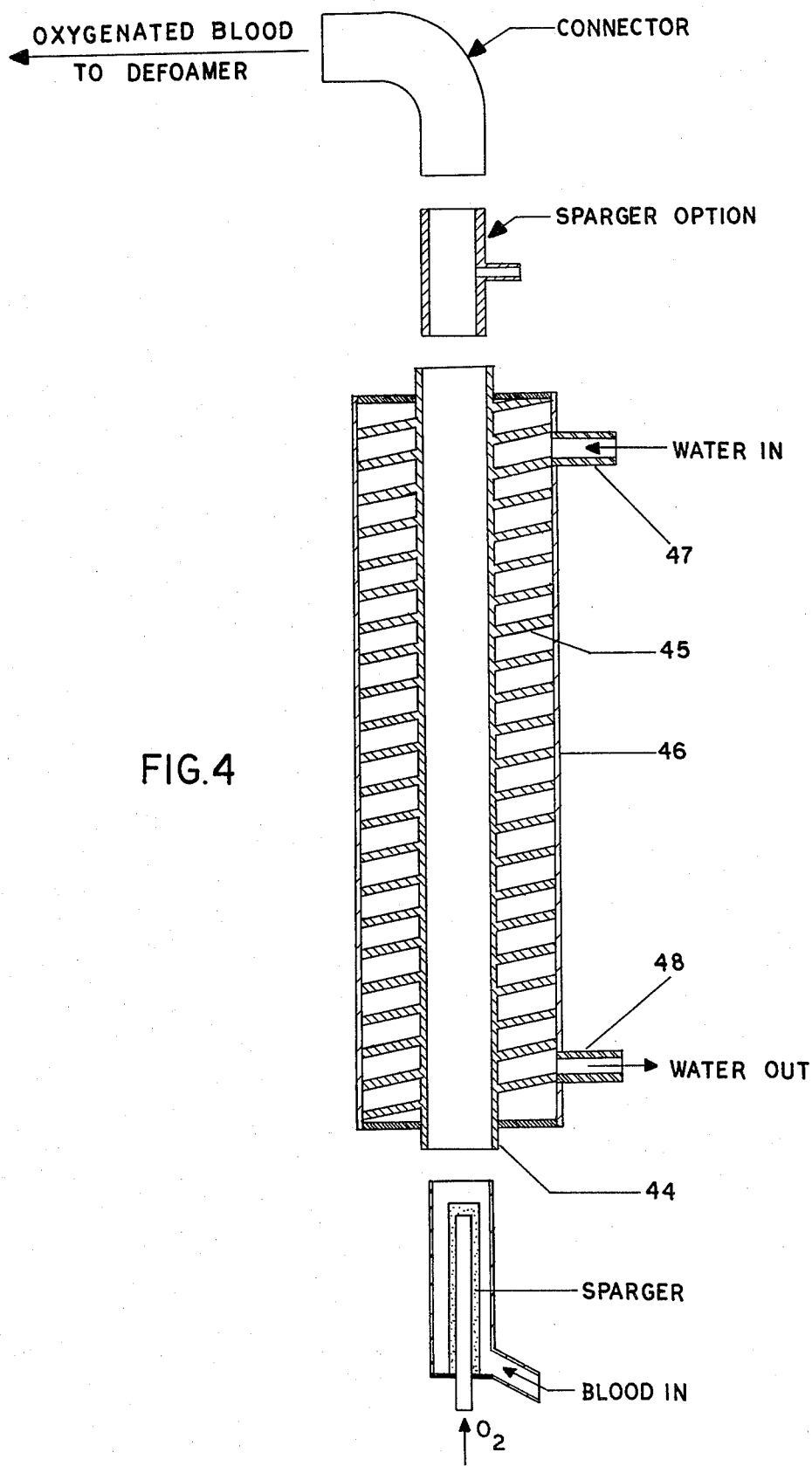

BLOOD OXYGENATOR

BACKGROUND OF THE INVENTION

This invention relates to a new and improved blood oxygenator device, and more specifically to a device which is inexpensive, easy to control and results in a reduction of embolii and hemolysis.

Blood oxygenators presently on the market have use in cardiovascular work and in research. Many of these devices have the drawback in that for oxygen flow rates of 3–8 liters/minute, the relation between $O_2$ uptake and blood flow varies in a non linear manner which changes rapidly with increasing $O_2$ flow rates.

Consequently, small changes in oxygen concentration at elevated flow rates will produce marked changes in the $CO_2/O_2$ respiratory quotient ratio which is optimally about 0.8; significant departure from the 0.8 value will adversely affect the overall performance of an oxygenator.

It would be desireable to provide an oxygenator that obtains blood cooling and warming efficiencies which are comparable to those of the prior art, but at much less expense. Also, it would be desireable to reduce hemolysis and embolii formation by a combination of lower $O_2$ inlet flows and more uniform $O_2$ bubble formation. Furthermore, an oxygenator is required in which operation of the overall system results in a fairly constant $CO_2/O_2$ relationship over the desired range of oxygenation flow rates (e.g. 1–8 liters/min.), which would permit the device to be controlled easier when varying oxygen levels at the inlet sparger.

THE INVENTION

According to the invention, a blood oxygenator is provided, comprising a finned heat exchanger including a central tube for transporting oxygenated blood, or a heat exchange medium such as water, and a plurality of heat exchanger fins attached to the central tube. In the preferred embodiment, a plurality of fins are attached lengthwise along the central tube, the blood is passed between the fins, and water is passed along the tube.

In another embodiment of the heat exchanger, the fins may be formed from a single plate strip spirally attached to the central tube, or alternatively, the fins may comprise a plurality of individual, circular plates.

The use of a finned, tubular heat exchanger is efficient, and also is inexpensive to produce. Because the bubbles formed at the porous, plastic sparger are of relatively constant size, the blood containing these bubbles can be readily cooled. Other types of spargers may employ sintered glass beads, porous ceramics, etc.

BRIEF DESCRIPTION OF THE DRAWINGS

FIG. 1 is a view in axial section of a blood oxygenator and a heat exchanger having longitudinal fins according to the invention;

FIG. 2 is a sectional view of the heat exchanger taken along the lines 2—2 of FIG. 1;

FIG. 4 is an axial view in longitudinal section showing a spirally wound plate, finned heat exchanger according to the invention, and an oxygen inlet sparger;

DESCRIPTION OF THE PREFERRED EMBODIMENT

Figure 3:
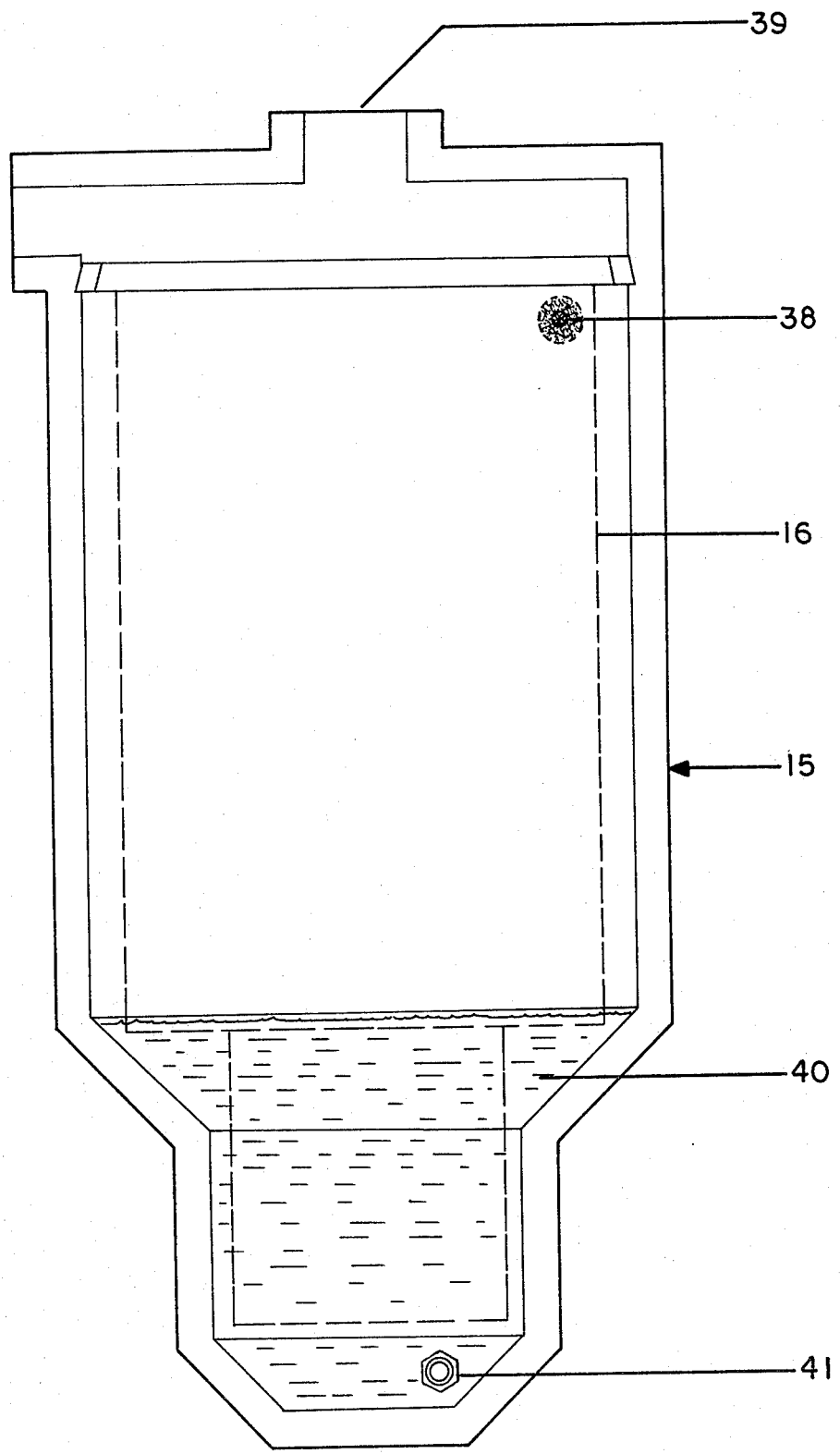
FIG. 3 is an external view in side elevation of a defoamer and degasser unit.

A blood oxygenator with a preferred type of heat exchanger 10, is shown in FIGS. 1 and 2 and comprises a heat exchange tube 11 mounted in a "LEXAN" polycarbonate reservoir 12 providing a sidewall 13 with indentations 14 on the sidewall interior. The reservoir 12 is integrally attached to a blood collection unit 15 which includes a cloth mesh blood defoamer bag 16 and a filler 17 in an arterial reservoir 18 of the collection unit 15. The filler may be sized to accommodate its use for adult, infants and pediatric, and its function is to raise the level of blood bubbles to the defoamer bag 16 and thereby reduce embolii formation. The filler also improves visibility of blood levels since it produces a white background against which the blood is viewed.

The heat exchange tube 11 is constructed of extruded aluminum which may be anodized to eliminate corrosion. The heat exchange tube includes interior, U-shaped channels 20, 21 providing for an in-out water flow, the ends of the channels being secured by an integral collar 22; a plurality of external, longitudinal fins 23 surround the channels.

Oxygenated blood flows in spaces 24 between the fins, and is cooled or warmed, depending on the medical condition of the patient. A clearance 25 is provided between the heat exchanger 10 and the sidewall 13 to maintain turbulent flow of the oxygenated blood and overcome stagnation problems such as dead spots, eddies, stratification, etc.; this is a significant problem of some oxygenators. A typical clearance 25 between the fins 23 and the sidewall 13 is about 40–110 mils, and the indentations 14 maintain the clearance uniform and improve turbulence.

Typical dimensions of the heat exchanger of FIG. 1 are about $1\frac{5}{8}$ to $2\frac{1}{4}$ inches when measured from the fin extremities along the minor and major axes of the heat exchanger in the cross section view of FIG. 2. Typical channel diameters are $\frac{1}{2}$ inches, and each fin (22 total) is about $\frac{1}{2}$ inches in depth; the overall length of the heat exchanger is about 13 inches; and, a 30° twist/foot may be imparted to the heat exchanger. While both heat exchangers shown in FIGS. 1 and 4 are adapted for cooling (or warming) blood during oxygenation, they also could be operated prior to, or subsequent to oxygenation. Furthermore, the finned heat exchangers of this invention may be usefully employed in other types of blood oxygenators.

Thus, the minimum heat exchange surface (in.$^2$) may be calculated as follows:

Fin area (in.$^2$) = number $\times$ 2 sides $\times$ length $\times$ width
       = $22 \times 2 \times 13 \times \frac{1}{2}$   = 286

Body area = $2 \times$ pi $\times$ radius $\times$ length
(rt. circ. cyl.)
(rt. elliptical) = $2 \times$ pi $\times (\frac{a+b}{2}) \times$ length
(cylinder)
   = $2$ pi $\frac{(2\frac{1}{4} - 1) + (1\frac{5}{8} - 1)}{2} \times 13$   = 76

End areas, neglecting fin edges   = 4

= 366 in.²

Figure 7:
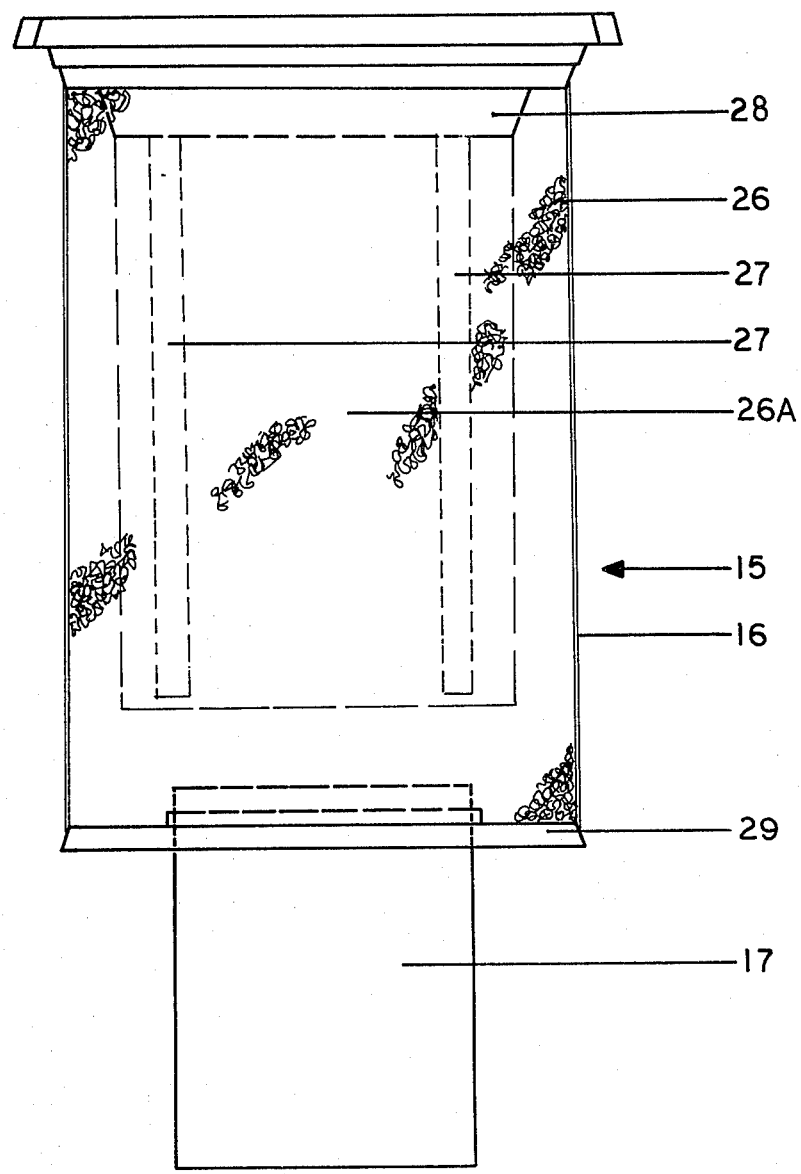
FIG. 7 is a front elevation view, partly in section of the defoaming portion of the oxygenator, showing the components thereof.

The blood collection unit 15 is shown in FIG. 7 and includes a polyurethane sponge 26 which is employed to support and expand the cloth defoamer bag 16. The sponge has a central cavity 26A through which oxygenated blood flows from the heat exchanger, and vertically aligned rods 27 are provided at either side of the sponge as a support. The sponge 26 at its upper side is provided with a funnel 28 which fits into the cavity 26A and permits blood to flow easily into the sponge from the heat exchange and oxygenating step. At its underside, the sponge bears against the filler 17 which is pressed in place by an extrusion 29. Thus the filler 17 and sponge 26 are both secured firmly in place between the upper end of the blood collection unit 15 and the lower end of the arterial reservoir 18.

The heat exchange unit 10 is provided at its lower end with a venous blood inlet 35 and an oxygen inlet 36. The oxygen inlet comprises a small bore inlet sparger tube 37 which is preferably made of a porous hydrophobic plastic material such as high density polyethylene, polypropylene, etc. Gas passes through the porous wall of the inlet sparger 37 and contacts the blood, forming bubbles as it flows past. Due to the hydrophobic and porous nature of the plastic, the wet oxygen bubbles will not adhere and coalesce together on the outside of the sparger tube wall, but will easily detach from the wall and remain small and of fairly uniform size. Typical sparger tube dimensions vary as follows: length, from about 20 mm to 50 mm; bore, from about 0.6 mm to 8.0 mm in diameter; and, wall thickness, from about 3 mm to 10 mm. Typical sparger pore sizes vary from about 150 to 250 microns. These porous tubes may be purchased from the Porex Division of Glass Rock Products, Fairburn, Ga. under the trade name of "POREX".

Figure 6B:
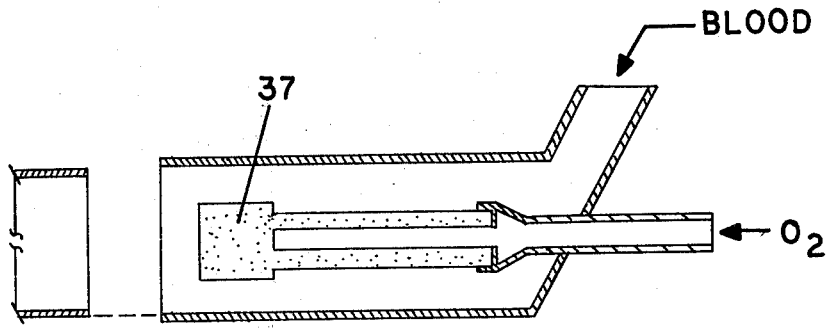
FIGS. 6A and 6B are enlarged views of the sparger and blood inlets.
Figure 6A:
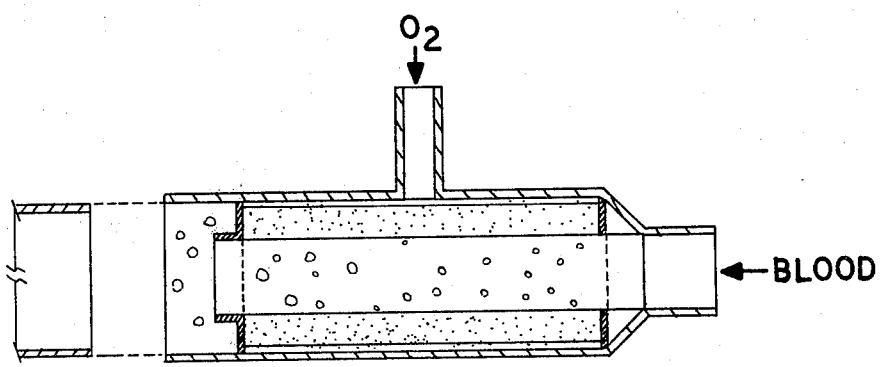

FIGS. 6A and 6B illustrate two types of sparger design. In one case, i.e. FIG. 6A, oxygen is fed from the outside of the sparger to the inside where it contacts blood flowing through the hollow interior of the sparger. In the other case, i.e. FIG. 6B, oxygen is fed through the hollow interior of the sparger and contacts blood as it flows past the outside walls of the sparger.

As shown in FIGS. 1, 3 and 7, temperature controlled, oxygenated blood from the heat exchange tube 10 is then fed to the blood collection unit 15 and passed through the fine cloth (e.g. nylon, polyester, etc.) mesh bag 16 where $CO_2$ is degassed and the blood is defoamed. Vent means 38 are employed to release the $CO_2$ and any other gases in the blood collection unit 15, and to maintain the gas pressure close to atmospheric. Scavenger means, not shown, connected to the vent may be employed to absorb anaesthetic gases, etc. If desired, a capped portion 39 may be utilized to seat a blood filter and/or cardiotomy reservoir using a snap-on, snap-off connection, quick lock, etc. These filters employ a non-woven mat of polyester fiber mat in conjunction with a nylon or polyester screen.

The defoamed, oxygenated blood with a physiological gas content is collected as a liquid 40 in the arterial reservoir 18 of the blood collection unit and then fed to the patient, test animal, etc. through an outlet tube 41; the blood is then returned from the patient into the oxygenator through the venous blood inlet 35.

Another form of heat exchanger of this invention is shown in FIG. 4 and comprises a hollow, heat exchange tube 44 having an attached, external, spirally wound plate 45 which functions as the heat exchange fins. This type of heat exchanger is both inexpensive and efficient; it can be purchased from the Noranda Metal Industries Forge-Fin Division and from Hudson Products. The heat exchange tube itself is constructed of aluminum and may have, say, a 20% twist to increase the residence time of the blood; the tube has a typical fin packing of about 4 to 10 per inch. As in the case of the heat exchanger shown in FIGS. 1 and 2, the heat exchanger of FIG. 4 may be of anodized aluminum to reduce corrosion.

The heat exchanger is mounted in a plastic, water-tight cylinder 46 such as "LEXAN" polycarbonate which forms a water reservoir; water is circulated through the cylinder via a water inlet tube 47 and outlet tube 48 countercurrent to the blood flow. For a given size of the tubes 47, 48 the inlet water flow may be easily adjusted to maintain the cylinder 46 totally filled. A suitable length of heat exchange tube 44 varies from about 4 to 16 inches, employing a tube hole diameter of about $\frac{3}{8}$ to 2 inches, and the water reservoir capacity may vary from about 100 cc to 500 cc.

Occasionally, it may be desireable to employ an oxygen inlet sparger at the outlet of the heat exchanger as shown in FIG. 4. A curved, tubular connector is used to forward oxygenated blood to a defoamer and collection unit.

Figure 5A:
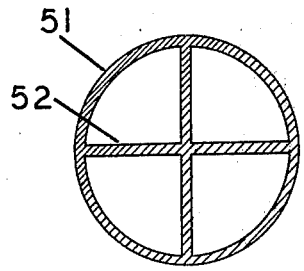
FIGS. 5A and 5B are cross section views of a spirally wound heat exchanger showing different internal tube designs.
Figure 5B:
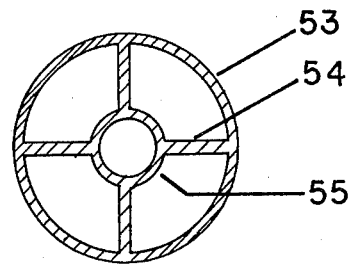

FIGS. 5A and 5B illustrate, in cross section, various tube structures. In FIG. 5A, the hollow tube 51 includes internal, spiral fins 52 which follow the 20% twist of the tube and which assist in the heat exchange operation. FIG. 5B shows, in cross section, the structure of another tube 53 having internal fins 54 mounted at right angles to each other and defining a central, hollow tube 55; this latter structure improves heat exchange along the tube axis. Both structures in FIGS. 5A and 5B preferably utilize the external, spirally wound plate 45 as the heat exchange fins.

The heat exchanger of this invention has use in blood oxygenator devices generally, and for other medical purposes such as in kidney dialysis, cardioplegic perfusion, isolated limb perfusion, isolated hypothermia and hyperthermia organ perfusions.

It will be appreciated that the heat exchanger of this invention may be altered from the description herein while still retaining its basic concept. As an example, the physical dimensions of both heat exchangers may be varied from those given to accommodate for its use with infants.

We claim:
1. A blood oxygenator, comprising:
 (a) i. a heat exchanger including an upright, longitudinal tubular body member formed from an integral aluminum extrusion;
   ii. a passageway within the tubular member for movement of a heat exchange fluid;
   iii. a plurality of parallel-like, generally radially directed, heat exchange fins formed longitudinally of the tubular member and along its exterior;
   iv. a plurality of channels, each defined between adjoining heat exchange fins and the tubular body, the channels being adapted for an unimpeded, upward flow of blood and oxygen in heat exchange relationship with the fluid, whereby the blood becomes oxygenated, the fins stabilizing the blood flow, thereby reducing hemolysis and improving oxygenation;

(b) a reservoir surrounding the fins, the reservoir being adapted to contain the blood surrounding the heat exchanger;

(c) a venous blood inlet to the reservoir for supplying to the reservoir, $CO_2$ rich blood for $O_2$ exchange;

(d) an inlet sparger to the reservoir for supplying oxygen to the blood;

(e) a defoamer means for defoaming and collecting oxygenated and degassed blood from the reservoir;

(f) vent means for releasing $CO_2$ and miscellaneous gases from the defoamer; and (g) an outlet for the oxygenated blood.

2. The oxygenator of claim 1 wherein said tubular member is a U-shaped tube, the heat exchanger being ellipsoid in horizontal cross section, the ellipse defining a major axis of about $2\frac{1}{4}$ inches and a minor axis of about $1\frac{5}{8}$ inches; the heat exchanger length being about 13 inches; the heat exchanger employing about 22 longitudinal fins about $\frac{1}{2}$ inch in depth.

3. The oxygenator of claim 1 in which the venous blood inlet and the sparger are positioned within a common inlet tube.

4. The oxygenator of claim 1 in which the sparger is mounted at the inlet of the tubular heat exchanger.

5. The oxygenator of claim 1 in which the sparger is made of a material selected from the class consisting of: polyethylene, polypropylene and polytetrafluoroethylene.

6. The oxygenator of claim 1 in which the sparger pore sizes vary from about at least 150–250 microns.

7. The oxygenator of claim 1 in which oxygenation means are provided upstream and downstream of the heat exchanger.

8. The blood oxygenator of claim 1, in which the sparger tube comprises a porous hydrophobic material with a minimum pore size of about 150 microns.

9. The blood oxygenator of claim 1, in which the sparger is selected from the class consisting of sintered glass beads and porous ceramics.

10. The blood oxygenator of claim 1, in which the heat exchange reservoir comprises a clear plastic.

11. The blood oxygenator of claim 1, in which the surface area of the heat exchanger is in excess of about 366 in.$^2$.

12. The blood oxygenator of claim 1, in which the surface area per lineal inch of heat exchanger is at least 28:1.

13. The blood oxygenator of claim 1, in which the heat exchanger is elliptically shaped in transverse cross section when viewed longitudinally along the heat exchanger.

14. The blood oxygenator of claim 1, comprising spacing means disposed on the reservoir, to produce a clearance between the heat exchanger and reservoir, thereby overcoming stagnation effects.

15. The blood oxygenator of claim 1, comprising a fluted passageway within the tubular member of the heat exchanger for movement of a heat exchange fluid.

16. A blood oxygenator, comprising:

(a) i. a heat exchanger including an upright, longitudinal tubular body member formed from an integral aluminum extrusion;

ii. a passageway within the tubular member for movement of a heat exchange fluid;

iii. a plurality of parallel-like, generally radially directed, heat exchange fins formed longitudinally of the tubular member and along its exterior;

iv. a plurality of channels, each defined between adjoining heat exchange fins and the tubular body, the channels being adapted for an unimpeded, upward flow of blood and oxygen in heat exchange relationship with the fluid, whereby the blood becomes oxygenated, the fins stabilizing the blood flow, thereby reducing hemolysis and improving oxygenation;

(b) a reservoir surrounding the fins, the reservoir being adapted to contain the blood surrounding the heat exchanger;

(c) a venous blood inlet to the reservoir for supplying to the reservoir, $CO_2$ rich blood for $O_2$ exchange;

(d) an inlet sparger to the reservoir for supplying oxygen to the blood;

(e) a defoamer means for defoaming and collecting oxygenated and degassed blood from the reservoir, the defoamer means being positioned above an arterial reservoir containing a filler element to displace blood into contact with the defoamer, thereby reducing emboli formation;

(f) vent means for releasing $CO_2$ and miscellaneous gases from the defoamer; and, (g) an outlet for the oxygenated blood.

17. The blood oxygenator of claim 16, in which the arterial reservoir is transparent.

18. The blood oxygenator of claim 16 in which the heat exchanger is elliptically shaped in transverse cross section when viewed longitudinally along the heat exchanger.

19. The blood oxygenator of claim 18, in which the heat exchanger includes a U-shaped tube for passage of a heat exchange fluid.

* * * * *